(12) United States Patent
Rolf et al.

(10) Patent No.: US 8,309,015 B2
(45) Date of Patent: Nov. 13, 2012

(54) ZIRCONIA BODY AND METHODS

(75) Inventors: Jacqueline C. Rolf, River Falls, WI (US); Martin Goetzinger, Eching a. Ammersee (DE); Holger Hauptmann, Sindelsdorf (DE); Peter Bissinger, Diessen (DE); Ruediger Franke, Seefeld (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/178,233

(22) Filed: Jul. 7, 2011

(65) Prior Publication Data

US 2011/0260349 A1  Oct. 27, 2011

Related U.S. Application Data

(62) Division of application No. 12/521,142, filed as application No. PCT/US2007/089057 on Dec. 28, 2007, now abandoned.

(60) Provisional application No. 60/882,714, filed on Dec. 29, 2006.

(51) Int. Cl.
*C04B 35/64* (2006.01)
*C04B 35/48* (2006.01)

(52) U.S. Cl. ............................ 264/681; 264/16; 501/103

(58) Field of Classification Search ................. 264/663, 264/664, 910
See application file for complete search history.

(56) References Cited

U.S. PATENT DOCUMENTS

| | | |
|---|---|---|
| 4,639,356 A | 1/1987 | O'Toole |
| 4,742,030 A | 5/1988 | Masaki |
| 4,788,045 A | 11/1988 | Colombet |
| 5,037,579 A | 8/1991 | Matchett |
| 5,238,625 A * | 8/1993 | Sakurai et al. ............... 264/621 |
| 5,453,262 A | 9/1995 | Dawson |
| 5,652,192 A | 7/1997 | Matson |
| 6,030,606 A | 2/2000 | Holmes |
| 6,087,285 A | 7/2000 | Oomichi |
| 6,376,590 B2 | 4/2002 | Kolb |
| 6,461,732 B1 | 10/2002 | Wittmann |
| 6,569,533 B1 | 5/2003 | Uchida |
| 6,713,421 B1 | 3/2004 | Hauptmann |
| 6,878,456 B2 | 4/2005 | Castro |
| 7,241,437 B2 | 7/2007 | Davidson |
| 7,429,422 B2 | 9/2008 | Davidson |
| 7,674,523 B2 | 3/2010 | Davidson |

(Continued)

FOREIGN PATENT DOCUMENTS

DE          69821701      12/2004

(Continued)

OTHER PUBLICATIONS

Adschiri, "Rapid and Continuous Hydrothermal Crystallization of Metal Oxide Particles in Supercritical Water", J. Am. Ceram. Soc., 1992, vol. 75, No. 4, pp. 1019-1022.

(Continued)

*Primary Examiner* — Matthew Daniels
*Assistant Examiner* — Erin Snelting
(74) *Attorney, Agent, or Firm* — Pamela L. Stewart

(57) ABSTRACT

A translucent zirconia sintered body, a dental article comprising a shaped, translucent zirconia body, a zirconia green body, and methods of making a translucent zirconia sintered body, methods of making a dental article comprising a shaped, translucent zirconia body, and methods of making a zirconia green body are described.

14 Claims, 1 Drawing Sheet

U.S. PATENT DOCUMENTS

| | | |
|---|---|---|
| 2002/0004544 A1 | 1/2002 | Kolb |
| 2003/0165680 A1 | 9/2003 | Brady |
| 2004/0168610 A1 | 9/2004 | Conrad |
| 2004/0192790 A1 | 9/2004 | Chiang |
| 2005/0059766 A1 | 3/2005 | Jones |
| 2005/0063898 A1 | 3/2005 | Ja Chisholm |
| 2005/0147702 A1 | 7/2005 | Higashi |
| 2005/0147838 A1 | 7/2005 | Olson |
| 2005/0148735 A1 | 7/2005 | Olson |
| 2006/0148950 A1 | 7/2006 | Davidson |
| 2006/0204676 A1 | 9/2006 | Jones |
| 2006/0204745 A1 | 9/2006 | Jones |
| 2010/0276374 A1 | 11/2010 | Kolb |

FOREIGN PATENT DOCUMENTS

| | | | |
|---|---|---|---|
| EP | 194191 | | 9/1986 |
| EP | 206780 | | 12/1986 |
| EP | 337472 | | 10/1989 |
| EP | 5247854 | | 9/1993 |
| EP | 5247865 | | 9/1993 |
| EP | 841304 | | 5/1998 |
| EP | 908425 | | 4/1999 |
| JP | 62153163 | A * | 7/1987 |
| JP | 11147772 | | 6/1999 |
| JP | 2003206137 | | 7/2003 |
| JP | 2004262694 | | 9/2004 |
| JP | 2004269331 | | 9/2004 |
| JP | 2006240928 | | 9/2006 |
| JP | 2008050247 | | 3/2008 |
| JP | 2008081325 | | 4/2008 |
| JP | 2008511524 | | 4/2008 |
| WO | WO 01/12132 | | 2/2001 |
| WO | WO 01/30702 | | 5/2001 |

OTHER PUBLICATIONS

Blumenthal, The Chemical Behavior of Zirconium, Chapter 8, "Carboxylates of Zirconium", pp. 311-338, D. Van Nostrand Company, Princeton, NJ, (1958).

Chaim, "Effect of Oxide Additives on Grain Growth During Sintering of Nanocrystalline Zirconia Alloys", Materials Letters, 1998, vol. 35, pp. 245-250.

Chen, "Sintering Dense Nanocrystalline Ceramics Without Final-stage Grain Growth", Nature, Mar. 9, 2000, vol. 404, pp. 168-171.

Dawson, "Hydrothermal Synthesis of Advanced Ceramic Powders", Ceramic Bulletin, 1988, vol. 67, No. 10, pp. 1673-1678.

Duran, "Preparation, Sintering and Properties of Translucent $Er_2O_3$-doped Tetragonal Zirconia", J. Am. Ceram. Soc., Nov. 1989, vol. 72, No. 11, pp. 2088-2093.

Jayaseelan, "High-Strength Porous Alumina Ceramics by the Pulse Electric Current Sintering Technique", J. Am. Ceram. Soc., 2002, vol. 85, No. 1, pp. 267-269.

Kim, "Lattice Parameters, Ionic Conductivities, and Solubility Limits in Fluorite-Structure $MO_2$ Oxide ($M = Hf^{4+}, Zr^{4+}, Ce^{4+}, Th^{4+}, U^{4+}$) Solid Solutions", J. Am. Ceram. Soc., 1989, vol. 72, No. 8, pp. 1415-1421.

Li, Compacting and Sintering Behavior of Nano $ZrO_2$ Powders, Scripta Materialia, May 18, 2001, vol. 44, Issues 8-9, pp. 2269-2272.

Mazdiyasni, "Cubic Phase Stabilization of Translucent Yttria-Zirconia at Very Low Temperatures", J. Am. Ceram. Soc., Oct. 1967, vol. 50, No. 10, pp. 532-537.

Provencher, "Contin: A General Purpose Constrained Regularization Program for Inverting Noisy Linear Algebraic and Integral Equations", Computer Physics Communications, 1982, vol. 27, pp. 229-242.

Srdić, "Sintering Behavior of Nanocrystalline Zirconia Prepared by Chemical Vapor Synthesis", J. Am. Ceram. Soc., 2000, vol. 83, No. 4, pp. 729-736.

Wolff, "Untersuchungen zur Herstellung von transparentem Zirkonoxid",Thesis, Universität des Saarlandes, Saarbrüken, Germany, 2005.

Int'l Search Report for Int'l Appln. No. PCT/US2007/089057, 3 pages.

Written Opinion of the ISA for Int'l Appln. No. PCT/US2007/089057, 6 pages.

* cited by examiner

ZIRCONIA BODY AND METHODS

CROSS REFERENCE TO RELATED APPLICATIONS

This application is a divisional application of U.S. application Ser. No. 12/521,142, filed Jun. 25, 2009, now abandoned which is the national stage filing under 35 U.S.C. 371 of International Application No. PCT/US2007/089057 filed Dec. 28, 2007, which claims the benefit of U.S. Provisional Application Ser. No. 60/882,714, filed Dec. 29, 2006, which is incorporated herein by reference in its entirety.

BACKGROUND

Ceramic bodies made from metal oxide powders have been used for some time in making dental articles, because of good biocompatibility and stability under load. These ceramic bodies have been typically processed by machining, for example, a green compact or a sintered body using a milling cutter. Green compacts have been made by compacting the metal oxide powder using cold isostatic or uniaxial pressing methods. After machining, the green compact must be sintered to achieve final properties. Sintered bodies have been made by hot isostatic processing whereby the starting metal oxide powder is simultaneously compacted and sintered.

Aluminum oxide has been particularly important, although zirconia has been considered, because it has greater mechanical strength than aluminum oxide. Tetragonal zirconia has exceptional mechanical strength due to a phase transformation mechanism that is triggered when a crack propagates into the material, causing the crack to be arrested. However, tetragonal zirconia is presently found to be opaque, thus limiting this material from applications requiring higher translucency, such as dental applications. Translucent cubic zirconia is known, but it has relatively low mechanical strength. Therefore, there is a continuing need for ceramic bodies that have both high strength and translucency.

SUMMARY

A translucent tetragonal zirconia body has now been developed. In one aspect, therefore, the present invention provides a translucent zirconia sintered body useful in dental articles. In one embodiment, there is provided a translucent zirconia sintered body comprised of primary particles and having a density of at least 99 percent of full density, the primary particles having:
  a major phase which is tetragonal zirconium oxide, and
  a size no greater than 100 nm; and
wherein the diameter of any pores which are present in the zirconia sintered body is not more than about 25 nm.

In another embodiment, there is provided a dental article comprising a shaped, translucent zirconia sintered body comprised of primary particles and having a density of at least 99 percent of full density, the primary particles having:
  a major phase which is tetragonal zirconium oxide, and
  a size no greater than 100 nm; and
wherein the diameter of any pores which are present in the translucent zirconia sintered body is not more than about 25 nm.

In another aspect, the present invention provides a zirconia green body useful for making translucent zirconia sintered bodies and dental articles. In one embodiment, there is provided a zirconia green body comprised of primary particles and having a density of at least 50 percent of full density, the primary particles having:
  a major phase which is tetragonal zirconium oxide, and
  a size no greater than 50 nm; and
wherein the diameter of any pores which are present in the green body is not more than about 30 nm.

In another aspect, the present invention provides methods of making translucent zirconia sintered bodies, zirconia green bodies, and dental articles.

In one embodiment, there is provided a method of making a translucent zirconia sintered body comprising:
  providing a zirconia green body comprised of primary particles and having a density of at least 50 percent of full density, the primary particles having:
    a major phase which is tetragonal zirconium oxide, and
    a size no greater than 50 nm; and
  wherein the diameter of any pores which are present in the green body is not more than about 30 nm; and
  sintering the zirconia green body at a temperature no greater than 1200° C. to provide a translucent zirconia sintered body comprised of primary particles and having a density of at least 99 percent of full density, the primary particles having:
    a major phase which is tetragonal zirconium oxide, and
    a size no greater than 100 nm; and
  wherein the diameter of any pores which are present in the translucent zirconia sintered body is not more than about 25 nm.

In another embodiment, there is provided a method of making a zirconia green body comprising:
  providing a zirconia sol comprising zirconia particles having an average primary particle size no greater than 50 nm;
  drying the zirconia sol to form a zirconia green body comprised of primary particles and having a density of at least 50 percent of full density, the primary particles having:
    a major phase which is tetragonal zirconium oxide, and
    a size no greater than 50 nm; and
  wherein the diameter of any pores which are present in the green body is not more than about 30 nm.

In another embodiment, there is provided a method of making a dental article comprising:
  providing a translucent zirconia sintered body comprised of primary particles and having a density of at least 99 percent of full density, the primary particles having:
    a major phase which is tetragonal zirconium oxide, and
    a size no greater than 100 nm; and
  wherein the diameter of any pores which are present is not more than about 25 nm; and
  shaping the translucent zirconia sintered body to provide a dental article.

In another embodiment, there is provided a method of making a dental article comprising:
  providing a zirconia green body comprised of primary particles and having a density of at least 50 percent of full density, the primary particles having:
    a major phase which is tetragonal zirconium oxide, and
    a size no greater than 50 nm; and
  wherein the diameter of any pores which are present in the zirconia green body is not more than about 30 nm;
  sintering the zirconia green body at a temperature no greater than 1200° C. and for a time sufficient to form a partially sintered zirconia green body;
  shaping the partially sintered zirconia green body; and
  sintering the shaped, partially-sintered zirconia green body to provide a dental article comprising a shaped, translucent zirconia sintered body comprised of primary particles and having a density of at least 99 percent of full density, the primary particles having:
    a major phase which is tetragonal zirconium oxide, and a size no greater than 100 nm; and wherein the diameter of any pores which are present in the shaped, translucent zirconia sintered body is not more than about 25 nm.

Definitions

As used herein, the term "translucent" refers to a percent light transmittance of at least 50% for wavelengths 350-700 nm through a 1 mm thickness of a ceramic body.

As used herein, the terms "sintered" and "sintering" refer to a reduction in size and/or number or the elimination of interparticle pores in a granular structure comprised of particles by heating without melting.

As used herein, the term "body" or variations thereof refers to a three-dimensional structure.

As used herein, the term "zirconia green body" refers to a three-dimensional granular structure comprised of zirconium oxide particles, which is not sintered or is partially sintered.

As used herein, the term "full density" refers to the density of a pore-free body.

As used herein, the term "major phase" refers to a crystal phase that is present in the primary particles in an amount such that this phase comprises more than 50% of the zirconium oxide in the primary particles.

As used herein, the term "primary particle size" refers to the size of a non-associated single crystal zirconia particle. X-ray Diffraction (XRD) can be used to measure the primary particle size.

As used herein, the term "sol" refers to a dispersion or suspension of colloidal particles in a liquid phase (e.g., aqueous medium). The particles in the sol are typically not agglomerated or aggregated.

As used herein, the term "zirconia" refers to various stoichiometries for zirconium oxides, most typically $ZrO_2$, and may also be known as zirconium oxide or zirconium dioxide. The zirconia may contain up to 30 weight percent of oxides of other chemical elements such as, for example, oxides of yttrium (e.g., $Y_2O_3$).

As used herein, the term "associated" refers to a grouping of two or more primary particles that are aggregated and/or agglomerated. Similarly, the term "non-associated" refers to groupings of two or more primary particles that are free from aggregation and/or agglomeration.

As used herein, the term "aggregation" refers to a strong association between primary particles. For example, the primary particles may be chemically bound to one another. The breakdown of aggregates into smaller particles (e.g., primary particles) is generally difficult to achieve.

As used herein, the term "agglomeration" refers to a weak association of primary particles. For example, the primary particles may be held together by charge or polarity. The breakdown of agglomerates into smaller particles (e.g., primary particles) is less difficult than the breakdown of aggregates into smaller particles.

As used herein, the term "hydrodynamic particle size" refers to the volume-average particle size of the zirconia particles in a liquid phase as measured by Photon Correlation Spectroscopy (PCS) using the method described herein.

As used herein, the term "hydrothermal" refers to a method of heating an aqueous medium, in a closed vessel, to a temperature above the normal boiling point of the aqueous medium at a pressure that is equal to or greater than the pressure required to prevent boiling of the aqueous medium.

The term "comprising" and variations thereof (e.g., having, comprises, etc.) do not have a limiting meaning where these terms appear in the description and claims.

Also herein, the recitations of numerical ranges by endpoints include all numbers subsumed within that range (e.g., at least 50 percent includes 50, 50.5, 55, 60, 67.5, 70, 73.8, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

DETAILED DESCRIPTION OF ILLUSTRATIVE EMBODIMENTS OF THE INVENTION

Figure 1:
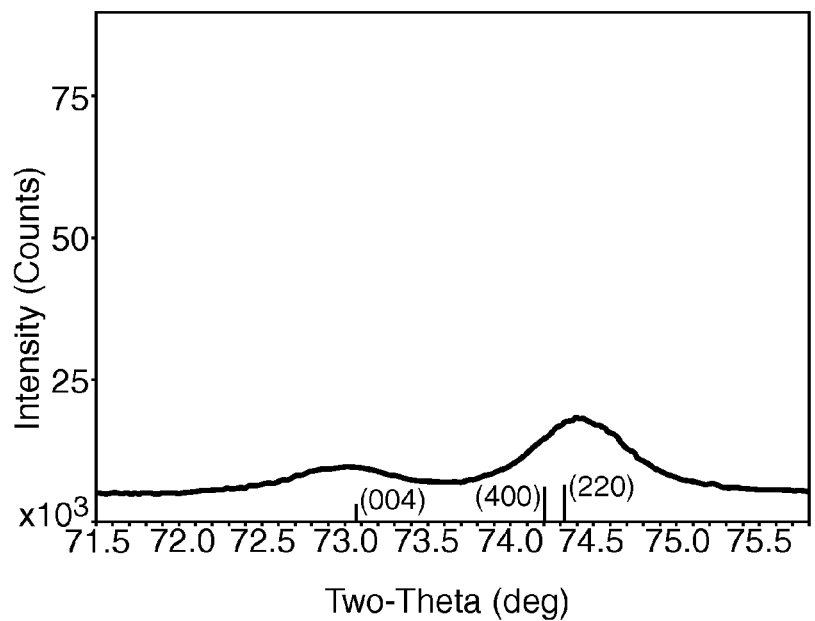
FIG. 1 is a representative x-ray diffraction pattern for an exemplary translucent zirconia sintered body having tetragonal zirconia as the major phase.

Until now, tetragonal zirconia bodies were obtainable only as an opaque material or a translucent material having a percent light transmittance of less than 40%. The opacity of previous tetragonal zirconia is attributed to light scattering caused by various lattice parameters of the crystal structure, as well as large particle and pore sizes in these bodies. However, a translucent zirconia sintered body comprising tetragonal zirconia can now be provided, at least in part, by making the size of the primary particles of the sintered body no greater than 100 nm. In one embodiment, therefore, the present invention provides a translucent zirconia sintered body comprised of primary particles and having a density of at least 99 percent of full density, the primary particles having:

a major phase which is tetragonal zirconium oxide, and a size no greater than 100 nm; and wherein the diameter of any pores which are present in the zirconia sintered body is not more than about 25 nm.

As the primary particle size is reduced relative to the wavelength of light being transmitted, light scattering caused by the primary particles can be minimized or even eliminated. For certain embodiments of the translucent zirconia sintered body, the primary particle size is preferably no greater than 50 nm. For certain of these embodiments, the primary particle size is no greater than 25 nm.

For certain embodiments, including any one of the above embodiments of the translucent zirconia sintered body, the percent light transmittance through a 1 mm thickness of the zirconia sintered body is at least 60% at 350-700 nm. For certain of these embodiments, the percent light transmittance is at least 70%.

The translucent zirconia sintered body can provide high flexural or bending strength because of the presence of tetragonal zirconia as the major crystal phase of the primary particles comprising the sintered body. For certain embodiments, including any one of the above embodiments of the translucent zirconia sintered body, the flexural strength of the zirconia sintered body is at least 600 MPa. For certain of these embodiments, the flexural strength of the zirconia sintered body is at least 800 MPa. For certain of these embodiments, the flexural strength of the zirconia sintered body is at least 1000 MPa. Flexural strength can be measured via a 3-point bend test per ASTM standard C1161. Dimensions of the test fixture and test specimen can be altered to accommodate other sizes of samples as long as the equations to calculate the strength values are corrected accordingly.

For certain embodiments, including any one of the above embodiments of the translucent zirconia sintered body, the major phase which is tetragonal zirconium oxide comprises at least 70 percent of the zirconium oxide in the primary particles. For certain of these embodiments, the major phase which is tetragonal zirconium oxide comprises at least 80 percent, at least 90 percent, at least 95 percent, or at least 99 percent of the zirconium oxide in the primary particles.

The amount of the zirconium oxide in the primary particles that is tetragonal zirconium oxide was determined using x-ray diffraction pattern analysis whereby the levels of tetragonal and cubic zirconia can be most easily distinguished by an examination of the positions of the tetragonal (220), tetragonal (400), and cubic (400) peaks that occur in the 71 to 76 degree (two-theta) scattering angle range. The tetragonal (220) and (400) peak positions provide direct evaluation of the tetragonal (a) and (c) lattice parameters, respectively, and the cubic (400) maximum provides direct evaluation of the cubic ($a_0$) lattice parameter. The lattice parameters are calculated from peak positions corrected by use of a silicon internal standard. By this analysis, the major zirconia phase present in the translucent zirconia sintered bodies appeared to be solely the tetragonal form as shown in the representative x-ray diffraction pattern of FIG. 1. There was no direct evidence for the presence of the cubic form of zirconia in the translucent zirconia sintered bodies, although with this analysis a small amount of cubic zirconia could be present.

The translucent zirconia sintered body has a low pore size, which is established during deposition of zirconia nanoparticles and is maintained through sintering. Light scattering resulting from the presence of large pores is, therefore, avoided in the present zirconia sintered body. For certain embodiments, the diameter of any pores which are present in the translucent zirconia sintered body is not more than about 20 nm. For certain embodiments, the diameter of any pores which are present in the translucent zirconia sintered body is not more than about 10 nm. For certain embodiments, the diameter of any pores which are present in the translucent zirconia sintered body is not more than about 5 nm.

The translucent zirconia sintered body can be shaped by conventional machining methods to provide a dental article. Accordingly, in another embodiment, there is provided a dental article comprising a shaped, translucent zirconia sintered body comprised of primary particles and having a density of at least 99 percent of full density, the primary particles having:

a major phase which is tetragonal zirconium oxide, and a size no greater than 100 nm; and wherein the diameter of any pores which are present in the translucent zirconia sintered body is not more than about 25 nm.

For certain embodiments of the dental article, the primary particle size of the shaped, translucent zirconia sintered body is no greater than 50 nm. For certain of these embodiments, the primary particle size is no greater than 25 nm.

For certain embodiments, including any one of the above embodiments of the dental article, the percent light transmittance through a 1 mm thickness of the translucent zirconia sintered body is at least 60% at 350-700 nm. For certain of these embodiments, the percent light transmittance is at least 70%.

For certain embodiments, including any one of the above embodiments of the dental article, the flexural strength of the translucent zirconia sintered body is at least 600 MPa. For certain of these embodiments, the flexural strength of the translucent zirconia sintered body is at least 800 MPa. For certain of these embodiments, the flexural strength of the zirconia sintered body is at least 1000 MPa.

For certain embodiments, including any one of the above embodiments of the dental article, the major phase which is tetragonal zirconium oxide comprises at least 70 percent of the zirconium oxide in the primary particles. For certain of these embodiments, the major phase which is tetragonal zirconium oxide comprises at least 80 percent, at least 90 percent, at least 95 percent, or at least 99 percent of the zirconium oxide in the primary particles.

For certain embodiments, including any one of the above embodiments of the dental article, the diameter of any pores which are present in the translucent zirconia sintered body is not more than about 20 nm. For certain of these embodiments, the diameter of any pores which are present in the translucent zirconia sintered body is not more than about 10 nm. For certain of these embodiments, the diameter of any pores which are present in the translucent zirconia sintered body is not more than about 5 nm.

The dental article in the above embodiments includes any format of a product for placement in the oral environment, wherein high flexural strength and translucency in the product are advantageous. For certain embodiments, the dental article is selected from the group consisting of a crown, a bridge, a framework, an abutment, an inlay, an onlay, an implant, and an orthodontic bracket. A framework includes a substructure, or part for a crown or bridge, for example, a coping for a crown. Additional material or structure, for example, a veneer, may be optionally applied to a framework prior to placement in the oral environment. For certain of these embodiments, the dental article is a crown, a bridge, or an abutment.

In another aspect, a new zirconia green body is provided, which is useful for making translucent zirconia sintered bodies and dental articles comprising the translucent zirconia sintered bodies. The new zirconia green body has a microstructure, including a low pore size and low primary particle size, that can ultimately serve as the basis for the translucency and strength properties of the above described translucent zirconia sintered body. Accordingly, in one embodiment, there is provided a zirconia green body comprised of primary particles and having a density of at least 50 percent of full density, the primary particles having:

a major phase which is tetragonal zirconium oxide, and a size no greater than 50 nm; and wherein the diameter of any pores which are present in the green body is not more than about 30 nm.

The low pore size contributes to a higher density. For certain embodiments, the zirconia green body has a density which is at least 65 percent of full density. For certain of these embodiments, the density is at least 75 percent of full density.

For certain embodiments, including any one of the above embodiments of the zirconia green body, the primary particle size is no greater than 25 nm.

For certain embodiments, including any one of the above embodiments of the zirconia green body, the diameter of any pores which are present in the green body is not more than about 25 nm. For certain of these embodiments, the diameter of any pores which are present in the green body is not more than about 20 nm.

For certain embodiments, including any one of the above embodiments of the zirconia green body, the major phase which is tetragonal zirconium oxide comprises at least 70 percent of the zirconium oxide in the primary particles of the zirconia green body. For certain of these embodiments, the major phase which is tetragonal zirconium oxide comprises at least 80 percent, at least 90 percent, at least 95 percent, or at least 99 percent of the zirconium oxide in the primary particles.

In another aspect, the present invention provides methods of making translucent zirconia sintered bodies, zirconia green bodies, and dental articles. Accordingly, in one embodiment, there is provided a method of making a translucent zirconia sintered body comprising:

providing a zirconia green body comprised of primary particles and having a density of at least 50 percent of full density, the primary particles having:
 a major phase which is tetragonal zirconium oxide, and
 a size no greater than 50 nm; and
wherein the diameter of any pores which are present in the green body is not more than about 30 nm; and sintering the zirconia green body at a temperature no greater than 1200° C. to provide a translucent zirconia sintered body comprised of primary particles and having a density of at least 99 percent of full density, the primary particles having:
 a major phase which is tetragonal zirconium oxide, and
 a size no greater than 100 nm; and
wherein the diameter of any pores which are present in the translucent zirconia sintered body is not more than about 25 nm. For certain of these embodiments, the zirconia green body is provided by providing a zirconia sol comprising zirconia particles having an average primary particle size no greater than 50 nm; and drying the zirconia sol to provide the zirconia green body.

In another embodiment, there is provided a method of making a zirconia green body comprising:

providing a zirconia sol comprising zirconia particles having an average primary particle size no greater than 50 nm;

drying the zirconia sol to form a zirconia green body comprised of primary particles and having a density of at least 50 percent of full density, the primary particles having:
 a major phase which is tetragonal zirconium oxide, and
 a size no greater than 50 nm; and
wherein the diameter of any pores which are present in the green body is not more than about 30 nm.

The zirconia sol comprising zirconia particles can be made as described in U.S. Patent Application Publication Nos. 2006/0148950 and 2006/0204745. Preparation of the zirconia sol is also described below.

For certain embodiments, the zirconia sol is provided containing zirconia particles dispersed in an aqueous medium that includes a carboxylic acid. The carboxylic acid contains no greater than four carbon atoms and is substantially free of a polyether carboxylic acid. For certain of these embodiments, the carboxylic acid is acetic acid.

For certain embodiments, including any one of the above embodiments where a zirconia sol containing zirconia particles is provided, the zirconia particles contain 0.1 to 8 weight percent yttrium based on the weight of the inorganic oxides in the zirconia particles.

For certain embodiments, including any one of the above embodiments where a zirconia sol containing zirconia particles is provided, the zirconia particles have an average primary particle size no greater than 40 nanometers. For certain of these embodiments, the average primary particle size is no greater than 30 nanometer. For certain of these embodiments, the average primary particle size is no greater than 25 nanometers. For certain of these embodiments, the average primary particle size is no greater than 20 nanometers. For certain of these embodiments, the average primary particle size is no greater than 10 nanometers. For certain of these embodiments, the average primary particle size is no greater than 5 nanometers. The primary particle size, which refers to the non-associated particle size of the zirconia particles, can be determined by x-ray diffraction For certain embodiments, including any one of the above embodiments where a zirconia sol containing zirconia particles is provided, the zirconia particles have a dispersion index of 1 to 5, a ratio of intensity-average particle size to volume-average particle size no greater than 3.0, and a crystal structure that is more than 50 percent tetragonal. For certain of these embodiments, the zirconia particles have a dispersion index of 1 to 3, a ratio of intensity-average particle size to volume-average particle size no greater than 3.0, and a crystal structure that is at least 70 percent tetragonal.

The particles of zirconia tend to exist in a substantially non-associated (i.e., non-aggregated and non-agglomerated) form in the sol. The extent of association between the primary particles can be determined from the hydrodynamic particle size. The hydrodynamic particle size is measured using Photon Correlation Spectroscopy and is described in more detail in the Examples section. The term "hydrodynamic particle size" and "volume-average particle size" are used interchangeably herein. If the particles of zirconia are associated, the hydrodynamic particle size provides a measure of the size of the aggregates and/or agglomerates of primary particles in the zirconia sol. If the particles of zirconia are non-associated, the hydrodynamic particle size provides a measure of the size of the primary particles.

A quantitative measure of the degree of association between the primary particles in the zirconia sol is the dispersion index. As used herein the "dispersion index" is defined as the hydrodynamic particle size divided by the primary particle size. The primary particle size (e.g., the weighted average crystallite size) is determined using x-ray diffraction techniques and the hydrodynamic particle size (e.g., the volume-average particle size) is determined using Photon Correlation Spectroscopy. As the association between primary particles in the sol decreases, the dispersion index approaches a value of 1. The zirconia particles typically have a dispersion index of 1 to 5, 1 to 4, 1 to 3, 1 to 2.5, or 1 to 2.

Photon Correlation Spectroscopy can be used to further characterize the zirconia particles in the sol. For example, the intensity of the light scattered by particles is proportion to the sixth power of the particle diameter. Consequently, the light-intensity distribution tends to be more sensitive to larger particles than smaller ones. The intensity-average size (e.g., measured in nanometers) is, in effect, the size of a particle that corresponds to the mean value of the light intensity distribution measured by the instrument. The zirconia particles tend to have an intensity-average size that is no greater than 70 nanometers, no greater than 60 nanometers, no greater than 50 nanometers, no greater than 40 nanometers, no greater than 35 nanometers, or no greater than 30 nanometers.

The light-intensity distribution obtained during analysis using Photon Correlation Spectroscopy can be combined with the refractive indices of the particles and the refractive index of the suspending medium to calculate a volume distribution for spherical particles. The volume distribution gives the percentage of the total volume of particles corresponding to particles of a given size range. The volume-average size is the size of a particle that corresponds to the mean of the volume distribution. Since the volume of a particle is proportional to the third power of the diameter, this distribution is less sensitive to larger particles than the intensity-average size. That is, the volume-average size will typically be a smaller value than the intensity-average size. The zirconia sols typically have a volume-average size that is no greater than 50 nanometers, no greater than 40 nanometers, no greater than 30 nanometers, no greater than 25 nanometers, no greater than 20 nanometers, or no greater than 15 nanometers. The volume-average size is used in the calculation of the dispersion index.

For a sample that has particles of only one size, the intensity-average size and volume-average size will be the same. Therefore, the ratio of the intensity-average size to the volume-average size gives a measure of the spread of sizes in the particles. Larger ratios correspond to broader particle size distributions. The zirconia particles typically have a ratio of intensity-average size (i.e., measured in nanometers) to volume-average size (i.e., measured in nanometers) that is no greater than 3.0, 2.5, 2.0, 1.8, 1.7, or 1.6.

The zirconia sols often have a high light transmittance due to the small size and non-associated form of the primary zirconia particles in the sol. High light transmittance of the sol can be desirable in the preparation of transparent or translucent materials such as ceramic bodies. As used herein, "light transmittance" refers to the amount of light that passes through a sample (e.g., a zirconia sol) divided by the total amount of light incident upon the sample and may be calculated as a percent using the following equation:

$$\text{Percent Transmittance} = 100(I/I_0)$$

where I is the light intensity passing though the sample and $I_0$ is the light intensity incident on the sample. The light transmittance of the zirconia sol may be determined using an ultraviolet/visible spectrophotometer set at a wavelength of 600 nanometers with a 1 cm path length.

The light transmittance is a function of the amount of zirconia in a sol. For zirconia sols having about 1 weight percent zirconia, the light transmittance is typically at least 70, 80, or 90 percent. For zirconia sols having about 10 weight percent zirconia, the light transmittance is typically at least 20, 50, or 70 percent.

Sintering additives can be used to act on and control the primary particle size during sintering. The sintering additive should be uniformly distributed throughout the zirconia green body. In one embodiment, a sintering additive is included with the zirconia sol. The sintering additive can be included, for example, during the preparation of the zirconia sol or added to the zirconia sol after the sol is prepared. For certain of these embodiments, a sintering additive is included with the zirconia sol, wherein the difference between the refractive index of the sintering additive and the refractive index of zirconia is less than 0.1. Alternatively, for certain of these embodiments, a sintering additive is included with the zirconia sol, wherein the sintering additive is selected from the group consisting of aluminum, niobium, calcium, and oxides thereof. For certain of these embodiments, the sintering additive is niobium or an oxide thereof.

The zirconia green body can be provided by drying the zirconia sol comprising zirconia particles. To obtain a crack-free body with a low pore size, the drying can be carried out slowly, at a low temperature, and/or at a high humidity, for example, at 20° C. and 80-90 percent relative humidity. For certain embodiments, including any one of the above embodiments which include drying the zirconia sol, drying the zirconia sol is carried out in a mold. The mold can be constructed from any of a variety of materials which are rigid or flexible, capable of containing the zirconia sol, and, preferably, which are essentially inert with respect to the zirconia sol. The mold can define the shape of the resulting green body. A wide range of shapes can be employed. For example the shape can be a three dimensional structure, such as a block, suitable for machining into a desired product shape. Alternatively, the shape can be such that, after sintering, a desired product shape is provided. For certain of these embodiments, for example, when a green body of about 5 mm by 5 mm by 5 mm or greater is desired, the mold has a diameter to height ratio of less than 2.

For certain embodiments, including any one of the above embodiments which include drying the zirconia sol in a mold, the mold is a flexible mold capable of accommodating the shrinkage of the zirconia sol during drying. As the volume of the drying zirconia sol is reduced, the volume of the mold is commensurately reduced, thereby minimizing or eliminating crack formation in the resulting green body. The mold may also apply a pressure greater than atmospheric pressure on the zirconia sol. Examples of flexible mold material include flexible membranes, which can be non-porous or nano-porous.

For certain embodiments, including any one of the above embodiments which include drying the zirconia sol in a mold, the mold is a nano-porous mold capable of wicking water out of the zirconia sol. The nano-porous mold can be rigid or flexible. Examples of nano-porous mold material include plaster of paris and nano-porous membranes with pore sizes less than the zirconia particle size.

To minimize crack formation and maximize the density of the zirconia green body, pressure can be applied during drying. This can be done as described above using a flexible mold. Alternatively, uniaxial pressure can be applied to the zirconia sol by opposing nano-porous punches within a nano-porous mold. The rate of water removal from the mold can be increased by placing the mold in warm circulating air or the like. In another alternative, the zirconia sol or a partially dried zirconia sol can be enveloped in a water permeable membrane to which isostatic pressure is applied by a hygroscopic fluid, such as glycerine, dimethylsulfoxide, or the like. The hygroscopic fluid can be heated to increase the rate of water removal from the sol. When using this water permeable membrane method, the sol is preferably partially dried (e.g., 1 to 10% water) prior to being placed within the water permeable membrane.

Electrophoretic deposition methods can also be used to produce zirconia green bodies with low pore size (and, therefore, high density). A membrane can be place in the zirconia sol with the major surfaces of the membrane facing opposing electrodes in the sol, and a potential difference (e.g., 5 to 30 V) can be applied across the membrane. The zirconia particles collect and build into a green body on the membrane. Use of the membrane avoids cracks and flaws caused by electrolysis of water that could occur during particle build at an electrode. In another alternative, the zirconia sol can be placed in a membrane reservoir (i.e., a reservoir defined by membrane walls), which in turn is placed in an electrolyte between two electrodes. Application of a potential difference (e.g., 3-70 V) causes zirconia particles to collect and build on the membrane surface, which is not in contact with the electrolyte.

Alternatively, for certain embodiments, drying the zirconia sol is carried out by spray drying to form a powder, and compacting the powder at an elevated temperature to form the green body. The zirconia sol can be atomized in a flame or in a hot wall reactor. Because of the elevated temperatures used (e.g., 600-1000° C.), bound acetic acid (or other carboxylic acids) is removed. The resulting dried powder is then compacted using suitable hot pressing method to form the zirconia green body.

For certain embodiments, including any one of the above embodiments which provides a green body, the density of the green body is at least 75 percent of full density.

For certain embodiments, including any one of the above embodiments which provides a green body, the primary particle size of the green body is no greater than 25 nm.

For certain embodiments, including any one of the above embodiments which provides a green body, the diameter of any pores which are present in the green body is not more than about 25 nm. For certain of these embodiments, the diameter of any pores which are present in the green body is not more than about 20 nm.

For certain embodiments, including any one of the above embodiments which provides a green body, the major phase which is tetragonal zirconium oxide comprises at least 70 percent of the zirconium oxide in the primary particles of the zirconia green body. For certain of these embodiments, the major phase which is tetragonal zirconium oxide comprises at least 80 percent, at least 90 percent, at least 95 percent, or at least 99 percent of the zirconium oxide in the primary particles.

The zirconia green body is sintered to provide the translucent zirconia sintered body. The primary particle size and growth of pores are limited during sintering, at least in part, by controlling the temperature and keeping the temperature from exceeding 1200° C. For certain embodiments, including any one of the above embodiments which provides a translucent zirconia sintered body, a temperature no greater than 1000° C. is used during sintering. For certain of these embodiments, a temperature no greater than 900° C. is used during sintering.

Several additional techniques can be considered for limiting the primary particle size and growth of pores during sintering. These include two-step sintering (e.g., using a higher temperature range for a shorter period of time and then a lower temperature range for a longer period of time), vacuum sintering, reactive gas sintering, electric field enhanced sintering (e.g., spark plasma sintering), hot uniaxial pressing, or hot isostatic pressing.

For certain embodiments, including any one of the above embodiments which provides a translucent zirconia sintered body, the primary particle size of the translucent zirconia sintered body is no greater than 50 nm. For certain of these embodiments, the primary particle size of the translucent zirconia sintered body is no greater than 25 nm.

For certain embodiments, including any one of the above embodiments which provides a translucent zirconia sintered body, the diameter of any pores which are present in the translucent zirconia sintered body is not more than about 20 nm. For certain of these embodiments, the diameter of any pores which are present in the translucent zirconia sintered body is not more than about 10 nm.

For certain embodiments, including any one of the above embodiments which provides a translucent zirconia sintered body, the percent light transmittance through a 1 mm thickness of the translucent zirconia sintered body is at least 60% at 350-700 nm.

For certain embodiments, including any one of the above embodiments which provides a translucent zirconia sintered body, the flexural strength of the translucent zirconia sintered body is at least 600 MPa. For certain of these embodiments, the flexural strength of the translucent zirconia sintered body is at least 800 MPa.

For certain embodiments, including any one of the above embodiments which provides a translucent zirconia sintered body, the major phase which is tetragonal zirconium oxide comprises at least 70 percent of the zirconium oxide in the primary particles of the translucent zirconia sintered body.

In another embodiment, the present invention provides a method of making a dental article comprising:

providing a translucent zirconia sintered body comprised of primary particles and having a density of at least 99 percent of full density, the primary particles having:
a major phase which is tetragonal zirconium oxide, and
a size no greater than 100 nm; and
wherein the diameter of any pores which are present is not more than about 25 nm; and
shaping the translucent zirconia sintered body to provide a dental article. For certain embodiments, the primary particle size is no greater than 50 nm. For certain of these embodiments, the primary particle size is no greater than 25 nm.

For certain embodiments, including any one of the above embodiments which provides a dental article, percent light transmittance through a 1 mm thickness of the translucent zirconia sintered body is at least 60% at 350-700 nm.

For certain embodiments, including any one of the above embodiments which provides a dental article, the flexural strength of the translucent zirconia sintered body is at least 600 MPa. For certain of these embodiments, the flexural strength of the translucent zirconia sintered body is at least 800 MPa.

For certain embodiments, including any one of the above embodiments which provides a dental article, the major phase which is tetragonal zirconium oxide comprises at least 70 percent of the zirconium oxide in the primary particles of the translucent sintered body.

For certain embodiments, including any one of the above embodiments which provides a dental article, the diameter of any pores which are present in the translucent zirconia sintered body is not more than about 20 nm. For certain of these embodiments, the diameter of any pores which are present in the translucent zirconia sintered body is not more than about 10 nm.

The translucent zirconia sintered body can be shaped using known methods of machining. For certain embodiments, including any one of the above embodiments which provides a dental article, shaping the translucent zirconia sintered body is carried out by milling. For certain of these embodiments, shaping the translucent zirconia sintered body is carried out by milling to a shape obtained by digital imaging.

For certain embodiments, including any one of the above embodiments which provides a dental article, the dental article is selected from the group consisting of a crown, a bridge, a framework, an abutment, an inlay, an onlay, an implant, and an orthodontic bracket.

In another embodiment, the present invention provides a method of making a dental article comprising:

providing a zirconia green body comprised of primary particles and having a density of at least 50 percent of full density, the primary particles having:
a major phase which is tetragonal zirconium oxide, and
a size no greater than 50 nm; and
wherein the diameter of any pores which are present in the zirconia green body is not more than about 30 nm;
sintering the zirconia green body at a temperature no greater than 1200° C. and for a time sufficient to form a partially sintered zirconia green body;
shaping the partially sintered zirconia green body; and
sintering the shaped, partially-sintered zirconia green body to provide a dental article comprising a shaped, translucent zirconia sintered body comprised of primary particles and having a density of at least 99 percent of full density, the primary particles having:
a major phase which is tetragonal zirconium oxide, and
a size no greater than 100 nm; and
wherein the diameter of any pores which are present in the shaped, translucent zirconia sintered body is not more than about 25 nm. For certain embodiments, the density of the green body is at least 65 percent of full density. For certain of these embodiments, the density of the green body is at least 75 percent of full density For certain embodiments, including any one of the above embodiments which includes partially sintering the zirconia green body, the primary particle size of the green body is no greater than 25 nm.

For certain embodiments, including any one of the above embodiments which includes partially sintering the zirconia green body, the diameter of any pores which are present in the green body is not more than about 25 nm. For certain of these embodiments, the diameter of any pores which are present in the green body is not more than about 20 nm.

For certain embodiments, including any one of the above embodiments which includes partially sintering the zirconia green body, sintering the zirconia green body is carried out at a temperature no greater than 1000° C. and for a time sufficient to form a partially-sintered zirconia green body. For certain of these embodiments, sintering the zirconia green body is carried out at a temperature no greater than 900° C. and for a time sufficient to form a partially-sintered zirconia green body. For certain of these embodiments, sintering the zirconia green body is carried out at a temperature no greater than 600° C. and for a time sufficient to form a partially-sintered zirconia green body.

For certain embodiments, including any one of the above embodiments which includes partially sintering the zirconia green body, the density of the partially-sintered zirconia green body is at least 75 percent of full density and less than 99 percent of full density.

For certain embodiments, including any one of the above embodiments which includes shaping the partially sintering the zirconia green body, shaping the partially-sintered zirconia green body is carried out by milling.

For certain embodiments, including any one of the above embodiments which includes shaping the partially sintering the zirconia green body, shaping the partially-sintered zirconia green body is carried out by milling to a shape obtained by digital imaging.

For certain embodiments, including any one of the above embodiments which includes sintering the shaped, partially-sintered zirconia green body to provide a dental article comprising a shaped, translucent zirconia sintered body, the primary particle size of the translucent zirconia sintered body is no greater than 50 nm. For certain of these embodiments, the primary particle size of the translucent zirconia sintered body is no greater than 25 nm.

For certain embodiments, including any one of the above embodiments which includes sintering the shaped, partially-sintered zirconia green body to provide a dental article comprising a shaped, translucent zirconia sintered body, the percent light transmittance through a 1 mm thickness of the translucent zirconia sintered body is at least 60% at 350-700 nm.

For certain embodiments, including any one of the above embodiments which includes sintering the shaped, partially-sintered zirconia green body to provide a dental article comprising a shaped, translucent zirconia sintered body, the flexural strength of the translucent zirconia sintered body is at least 600 MPa. For certain of these embodiments, the flexural strength of the translucent zirconia sintered body is at least 800 MPa.

For certain embodiments, including any one of the above embodiments which includes sintering the shaped, partially-sintered zirconia green body to provide a dental article comprising a shaped, translucent zirconia sintered body, the major phase which is tetragonal zirconium oxide comprises at least 70 percent of the zirconium oxide in the primary particles of the translucent zirconia sintered body.

For certain embodiments, including any one of the above embodiments which includes sintering the shaped, partially-sintered zirconia green body to provide a dental article comprising a shaped, translucent zirconia sintered body, the diameter of any pores which are present in the translucent zirconia sintered body is not more than about 20 nm. For certain of these embodiments, the diameter of any pores which are present in the translucent zirconia sintered body is not more than about 10 nm.

For certain embodiments, including any one of the above embodiments which includes sintering the shaped, partially-sintered zirconia green body to provide a dental article comprising a shaped, translucent zirconia sintered body, the dental article is selected from the group consisting of a crown, a bridge, a framework, an abutment, an inlay, an onlay, an implant, and an orthodontic bracket.

Preparation of the Zirconia Sol

The zirconia sol comprising zirconia particles can be made by preparing a first feedstock that contains a zirconium salt and subjecting the first feedstock to a first hydrothermal treatment to form a zirconium-containing intermediate. A second feedstock is then formed by removing at least a portion of any byproduct formed in the first hydrothermal treatment and subjecting the second feedstock to a second hydrothermal treatment to form a zirconia sol that contains the zirconia particles.

The first feedstock is prepared by forming an aqueous precursor solution that contains a zirconium salt. The anion of the zirconium salt is usually chosen so that it can be removed during subsequent steps in the process for preparing the zirconia sol. Additionally, the anion is often chosen to be non-corrosive, allowing greater flexibility in the type of material chosen for the processing equipment such as the hydrothermal reactors.

The anion of the zirconium salt is usually a carboxylate. At least 50 mole percent of the carboxylate anions have no greater than four carbon atoms. For example, in some precursor solutions, at least 60, 70, 80, 90, 95, 98, or 99 mole percent of the carboxylate anions have no greater than four carbon atoms.

Suitable carboxylates having no greater than four carbon atoms include formate, acetate, propionate, butyrate, or a combination thereof. These carboxylate anions can often be removed during the process by conversion to the corresponding volatile acid.

In some precursor solutions, the anion is a mixture of a carboxylate having no greater than four carbon atoms and a polyether carboxylate anion. Suitable polyether carboxylate anions are the corresponding weak bases of water-soluble monocarboxylic acids (i.e., one carboxylic acid group per molecule) having a polyether tail. The polyether tail contains repeating difunctional ether radicals having the general formula —O—R— where R is an alkylene group such as, for example, methylene, ethylene and propylene (including n-propylene and iso-propylene) or a combination thereof. Suitable polyether carboxylates have more than four carbon atoms and include, but are not limited to, those formed from polyether carboxylic acids such as 2-[2-(2-methoxyethoxy) ethoxy]acetic acid (MEEAA) and 2-(2-methoxyethoxy)acetic acid (MEAA). The polyether carboxylate, if included in the precursor solution, is typically present in an amount no greater than 50 mole percent based on the moles of carboxylate anions in the precursor solution. For example, the amount of polyether carboxylate can be no greater than 40, 30, 20, 10, 5, 2, or 1 mole percent of the carboxylate anions in the precursor solution.

Some precursor solutions are substantially free of polyether carboxylates, substantially free of carboxylates that have more than four carbon atoms, or a combination thereof. As used herein, the term "substantially free of polyether carboxylates" means that less than 1 mole percent of the carboxylate in the precursor solution are polyether carboxylates or the corresponding polyether carboxylic acid. For example, less than 0.5, 0.2, or 0.1 mole percent of the carboxylates in the precursor solution are polyether carboxylates or the corresponding polyether carboxylic acid. As used herein, the term "substantially free of carboxylates that have more than four carbon atoms" means that less than 1 mole percent of the carboxylates or the corresponding carboxylic acids in the precursor solution have greater than four carbon atoms. For example, less than 0.5, 0.2, or 0.1 mole percent of the carboxylates or corresponding carboxylic acids have greater than four carbon atoms.

Some precursor solutions are substantially free of halides such as chlorides. As used herein, the term "substantially free of halides" means that the precursor solution has less than $10^{-2}$, $10^{-3}$, $10^{-4}$, or $10^{-5}$ moles/liter halide.

The zirconium salt is often zirconium acetate. Zirconium acetate can be represented by a formula such as $ZrO_{((4-n)/2)}{}^{n+}(CH_3COO^-)_n$ where n is in the range of 1 to 2. The zirconium ion may be present in a variety of structures depending, for example, on the pH of the precursor solution. Methods of making zirconium acetate are described, for example, in W. B. Blumenthal, "The Chemical Behavior of Zirconium," pp. 311-338, D. Van Nostrand Company, Princeton, N.J. (1958). Suitable aqueous solutions of zirconium acetate are commercially available, for example, from Magnesium Elektron, Inc. (Flemington, N.J.) that contain up to 17 weight percent zirconium, up to 18 weight percent zirconium, up to 20 weight percent zirconium, or up to 22 weight percent zirconium.

Some precursor solutions contain a yttrium salt in addition to a zirconium salt. As with the zirconium salt, the anion of the yttrium salt is typically chosen to be removable during subsequent processing steps and to be non-corrosive. The anion of the yttrium salt is often a carboxylate having no more than four carbon atoms. For example, the anion can be acetate. The yttrium salt is often present in an amount up to 0.12, 0.10, 0.08, 0.06, or 0.04 grams yttrium per gram of zirconium.

The liquid phase of the precursor solution is typically predominately water. However, other miscible co-solvents can be included in the liquid phase in amounts up 20 weight percent based on the weight of the liquid phase. Suitable co-solvents include, but are not limited to, 1-methoxy-2-propanol, ethanol, isopropanol, ethylene glycol, N,N-dimethylacetamide, and N-methylpyrrolidone.

In some embodiments, the first feedstock is prepared by forming an aqueous precursor solution that includes a zirconium salt and an optional yttrium salt and then removing at least a portion of the anions in the precursor solution. Any suitable method known in the art for removing a portion of the anions can be used. Removal methods include, but are not limited to, vaporization, dialysis, ion exchange, precipitation, filtration, and the like. In some removal methods, the anion is removed as an acid. Although not wanting to be bound be theory, the partial removal of the anion in the precursor solution may reduce the formation of agglomerates and aggregates during one or more of the subsequent hydrothermal treatment steps.

In one method of at least partially removing the anions in the precursor solution, the precursor solution can be heated to vaporize an acidic form of the anion. For example, a carboxylate anion having no more than four carbon atoms can be removed as the corresponding carboxylic acid. More specifically, an acetate anion can be removed as acetic acid. The heating also can at least partially remove the liquid phase (e.g., aqueous medium) of the precursor solution in addition to the carboxylic acid. The partial removal of the liquid phase results in the formation of a concentrated precursor. In some methods, the solids can be increased up to 25, 50, 75, or 100 weight percent. The concentrated precursor often contains at least 10, 15, 20, 25, 30, 35, or 40 weight percent zirconium. For example, the concentrated precursor can contain 11 to 43 weight percent zirconium or 21 to 43 weight percent zirconium.

All or a portion of the liquid phase removed to form the concentrated precursor can be replaced prior to the first hydrothermal treatment. The concentrated precursor can be diluted with water (e.g., deionized water) to provide the first feedstock. The first feedstock can have a solid content that is lower than the solid content of the precursor solution, equal to the solid content of the precursor solution, or greater than the solid content of the precursor solution.

The first feedstock typically has solids in the range of 0.5 to 20 weight percent or 2 to 15 weight percent. The first feedstock often contains at least 0.2, 0.5, 1, or 2 weight percent zirconium. In some embodiments, the first feedstock contains up to 6, 8, or 9 weight percent zirconium. For example, the first feedstock often contains 0.2 to 9 weight percent zirconium or 1 to 6 weight percent zirconium.

The pH of the first feedstock is typically in the acidic range. For example, the pH is usually less than 6, 5, 4, or 3.

The first feedstock is subjected to a first hydrothermal treatment. The zirconium species in the first feedstock undergoes partial hydrolysis to form a zirconium-containing intermediate and a byproduct. Likewise, any optional yttrium salt present in the first feedstock can undergo partial hydrolysis. The hydrolysis reaction is often accompanied by the release of an acidic byproduct when the anion is a carboxylate. For example, if the anion is formate, acetate, propionate, or butyrate, the corresponding acid (i.e., formic acid, acetic acid, propionic acid, or butyric acid respectively) can be released during the hydrolysis reaction.

The hydrothermal treatments can be in a batch reactor or a continuous reactor. The residence times are typically shorter and the temperatures are typically higher in a continuous reactor compared to a batch reactor. The time of the hydrothermal treatments can be varied depending on the temperature of the reactor and the concentration of the feedstock. The pressure in the reactor can be autogenous (i.e., the vapor pressure of water at the temperature of the reactor), can be hydraulic (i.e., the pressure caused by the pumping of a fluid against a restriction), or can result from the addition of an inert gas such as nitrogen or argon. Suitable batch hydrothermal reactors are available, for example, from Parr Instruments Co. (Moline, Ill.). Suitable continuous hydrothermal reactors are described, for example, in U.S. Pat. Nos. 5,453,262 (Dawson et al.) and 5,652,192 (Matson et al.); Adschiri et al., J. Am. Ceram. Soc., 75, 1019-1022 (1992); and Dawson, Ceramic Bulletin, 67 (10), 1673-1678 (1988).

In some methods, at least one of the hydrothermal treatments is in a continuous reactor. For example, the first hydrothermal treatment can be in a continuous reactor while the second hydrothermal treatment is in a batch reactor. In another example, the first hydrothermal treatment can be in a batch reactor while the second hydrothermal treatment is in a continuous reactor. In still another example, both the first and second hydrothermal treatments are in a continuous reactor.

The first hydrothermal treatment can be in a batch reactor at a temperature in the range of 150° C. to 300° C., in the range of 155° C. to 250° C., or in the range of 160° C. to 200° C. In some first hydrothermal treatments in a batch reactor, the reactor is heated to the desired temperature and then cooled immediately. It may take, for example, about 1 hour to reach the desired temperature. In other first hydrothermal treatments in a batch reactor, the reaction temperature is held for at least 0.5, 0.75, 1, or 2 hours. The time at the reaction temperature can be up to 3, 3.5, 4, 5, 6, or 8 hours in a batch reactor. For example, the time the reaction temperature is held can be 0.25 to 8 hours, 0.5 to 6 hours, or 0.75 to 3.5 hours.

Alternatively, the first hydrothermal treatment can be in a continuous reactor at a temperature in the range of 150° C. to 300° C., in the range of 160° C. to 250° C., in the range of 170° C. to 220° C., or in the range of 180° C. to 215° C. for a period of at least 1 minute. In some continuous reactors, the residence time is at least 2, 3, 3, 5, or 4 minutes. The residence time can be up to 8, 10, 12, 15, or 20 minutes in a continuous reactor. For example, the residence time in a continuous reactor can be 1 to 20 minutes, 2 to 15 minutes, or 3 to 10 minutes.

The zirconium salts and optional yttrium salts in the first feedstock undergo only partial hydrolysis during the first hydrothermal treatment. The product of the first hydrothermal treatment includes a zirconium-containing intermediate plus various byproducts in a liquid phase. If an optional yttrium salt is included in the first feedstock, the zirconium-containing intermediate also contains yttrium. The zirconium-containing intermediate is only partially hydrolyzed and is not crystalline zirconia. The zirconium-containing intermediate is essentially amorphous based on x-ray diffraction analysis. That is, the x-ray diffraction pattern for the zirconium-containing intermediate tends to have broad peaks rather than the relatively narrow peaks indicative of crystalline material. The percent conversion (i.e., the extent of hydrolysis) can be calculated, for example, using Thermal Gravimetric Analysis (TGA). This method of calculating the percent conversion is particularly suitable when the carboxylate anions in the first feedstock are free of polyether carboxylates, free of carboxylates having more than four carbon atoms, or combinations thereof. The percent conversion of the zirconium-containing intermediate can be given by the following equation % Conversion=$100(A-B)/(A-C)$ where A is the percent weight loss of the first feedstock, B is the percent weight loss of the zirconium-containing intermediate, and C is the percent weight loss of the zirconia sol. The percent weight loss for the first feedstock, the intermediate, and the zirconia sol is determined by drying each sample at 120° C. for 30 minutes before analysis. After equilibration at 85° C. in the thermal gravimetric analyzer, each sample is heated at a rate of 20° C./minute to 200° C. The temperature is held at 200° C. for 20 minutes, increased at a rate of 20° C./minute to 900° C., and held at 900° C. for 20 minutes. The percent weight loss can be calculated from the following equation % weight loss=$100(\text{weight}_{200C}-\text{weight}_{900C})/\text{weight}_{900C}$ for the first feedstock, the zirconium-containing intermediate, and the zirconia sol. The percent weight loss corresponds to what is not an inorganic oxide in each of the dried samples.

The percent conversion of the zirconium-containing intermediate is typically 40 to 75 percent. In some methods, the percent conversion of the zirconium-containing intermediate is 45 to 70 percent, 50 to 70 percent, 55 to 70 percent, or 55 to 65 percent. The percent conversion can be used to select suitable conditions for the first hydrothermal treatment.

If the hydrolysis reaction during the first hydrothermal treatment is allowed to proceed to produce a zirconium-containing intermediate with a percent conversion greater than about 75 percent, the final zirconia sol tends to contain associated (e.g., aggregated and/or agglomerated) rather than non-associated primary particles of zirconia. Although not wanting to be bound by theory, it is advantageous to remove at least a portion of the byproducts of the hydrolysis reaction during the course of the reaction. Thus, it is advantageous to subject the first feedstock to a first hydrothermal treatment and remove a portion of the byproduct prior to the second hydrothermal treatment.

The second feedstock, the material that is subjected to the second hydrothermal treatment, is prepared from the product of the first hydrothermal treatment. The preparation of the second feedstock usually involves removing at least some of the byproducts that are produced during the first hydrothermal treatment. An acid, which can be formed from the anion of the zirconium salt and the optional yttrium salt, is often one of the byproducts of the first hydrothermal treatment. When the acidic byproduct is a carboxylic acid having no more than four carbon atoms, the acid can be removed by a variety of methods such as vaporization, dialysis, ion exchange, precipitation, filtration, and the like.

The removal of at least some of the byproducts of the first hydrothermal treatment also can result in the removal of at least some of the liquid phase (e.g., aqueous medium). That is, an intermediate concentrate can be formed. In some embodiments, only a portion of the liquid phase is removed (i.e., the intermediate concentrate has a liquid phase). For example, some products of the first hydrothermal treatment contain a solid phase that can be separated from part of the liquid phase (e.g., the solid phase can settle out of the liquid phase). At least a portion of the liquid phase can be removed by methods such as by siphoning, decantation, or centrifugation. In other embodiments, the product of the first hydrothermal treatment is dried to form a residue (i.e., the intermediate concentrate has little or no liquid phase). The solids of the intermediate concentrate are often in the range of 10 to 100 weight percent.

The intermediate concentrate typically contains at least 5, 8, 10, 20, or 30 weight percent zirconium. The intermediate concentrate can contain up to 30, 40, 50, or 52 weight percent zirconium. For example, the intermediate concentrate can contain 5 to 52 weight percent zirconium or 8 to 52 weight percent zirconium.

The intermediate concentrate, if the solids are no greater than 50 weight percent, can be used as the second feedstock. Alternatively, the intermediate concentrate can be diluted with water (e.g., deionized water) to form the second feedstock. The second feedstock often contains 0.5 to 50 weight percent solids or 3 to 40 weight percent solids when the second hydrothermal reactor is a batch reactor. The second feedstock often contains 0.5 to 25 weight percent solids or 7 to 22 weight percent solids when the second hydrothermal reactor is a continuous reactor.

The second feedstock typically contains at least 0.3 weight percent zirconium. When the second reactor is a batch reactor, the second feedstock often contains at least 0.5, 1, or 2 weight percent zirconium. The second feedstock for a batch reactor can contain up to 15, 20, 21, 25, or 26 weight percent zirconium. For example, the second feedstock for a batch reactor can contain 0.3 to 26 weight percent zirconium or 2 to 21 weight percent zirconium. When the second reactor is a continuous reactor, the second feedstock often contains at least 1, 2, 4, or 8 weight percent zirconium. The second feedstock for a continuous reactor often contains up to 11, 12, or 13 weight percent zirconium. For example, the second feedstock for a continuous reactor can contain 0.3 to 13 weight percent zirconium or 8 to 11 weight percent zirconium.

The pH of the second feedstock is typically less than 7. For example, the second feedstock can have a pH that is no greater than 6 or no greater than 5.

The second feedstock is subjected to a second hydrothermal treatment to form a zirconia sol. If a batch reactor is used for the second hydrothermal treatment, the reaction temperature is often in the range of 150° C. to 300° C., in the range of 160° C. to 250° C., or in the range of 175° C. to 200° C. for a period of at least 30 minutes. In some batch reactors, the residence time is at least 1 hour, 2, or 4 hours. The residence time can be up to 8, 10, 12, 14, 16, 18, or 24 hours in a batch reactor. For example, the residence time in a batch reactor can be 0.5 to 24 hours, 1 to 18 hours, or 1 to 14 hours. Alternatively, the second hydrothermal treatment can be in a continuous reactor at a temperature in the range of 150° C. to 300° C., in the range of 160° C. to 250° C., in the range of 180° C. to 220° C., or in the range of 200° C. to 215° C. for a period of at least 1 minute. In some continuous reactors, the residence time is at least 1, 2, 5, or 10 minutes. The residence time can be up to 60, 80, 90, 100, or 120 minutes in a continuous reactor. For example, the residence time in a continuous reactor can be 1 to 120 minutes, 5 to 100 minutes, or 10 to 90 minutes.

During the second hydrothermal treatment, the zirconium-containing intermediate undergoes further hydrolysis. The product of the second hydrothermal treatment is a zirconia sol that contains crystalline zirconia particles. The zirconia sol can be dried at a temperature of 120° C. to provide zirconia particles that typically contains 75 to 95 weight percent inorganic oxides. The zirconia particles can contain yttrium oxide (i.e., $Y_2O_3$) in addition to zirconia (i.e., $ZrO_2$). The zirconia particles can also contain some organic material, for example, by surface treating the zirconia particles.

In some embodiments, the zirconia sol is further treated to at least partially remove the byproducts formed during the second hydrothermal treatment. The byproducts are often acids formed from the anion of the zirconium salt or the optional yttrium salt. It is often desirable to remove the acidic byproduct if the zirconia particles in the zirconia sol will be combined with an organic matrix to form a composite material. For example, the acidic byproduct can be a carboxylic acid that can be removed by vaporization, ion exchange, precipitation, or dialysis. The zirconia sol often contains 0.5 to 55 weight percent solids or 2 to 51 weight percent solids.

The zirconia sol typically contains at least 0.3 weight percent zirconium. For example, the zirconia sol can contain at least 1, 2, 5, or 10 weight percent zirconium. The zirconia sol often contains up to 34, 35, or 37 weight percent zirconium. For example, the zirconia sol can contain 0.3 to 37 weight percent zirconia, 0.5 to 35 weight percent zirconium, or 1 to 34 weight percent zirconium.

The zirconia sol is prepared using at least two hydrothermal treatments. In some embodiments, more than two hydrothermal treatments are used. Between each hydrothermal treatment, at least some of the acidic byproducts formed in the preceding hydrothermal treatment can be removed.

Objects and advantages of this invention are further illustrated by the following examples, but the particular materials and amounts thereof recited in these examples, as well as other conditions and details, should not be construed to unduly limit this invention.

EXAMPLES

All parts, percentages, ratios, etc. in the examples and the rest of the specification are by weight, unless noted otherwise.

Solvents and other reagents used were obtained from Sigma-Aldrich Chemical Company; Milwaukee, Wis. unless otherwise noted.

Test Methods

Photon Correlation Spectroscopy (PCS)

The volume-average particle size was determined by Photon Correlation Spectroscopy (PCS) using a Malvern Series 4700 particle size analyzer (available from Malvern Instruments Inc., Southborough, Mass.). Dilute zirconia sol samples were filtered through a 0.2 µm filter using syringe-applied pressure into a glass cuvette that was then covered. Prior to starting data acquisition the temperature of the sample chamber was allowed to equilibrate at 25° C. The supplied software was used to do a CONTIN analysis with an angle of 90 degrees. CONTIN is a widely used mathematical method for analyzing general inverse transformation problems that is further described in S. W. Provencher, *Comput. Phys. Commun.*, 27, 229 (1982). The analysis was performed using 24 data bins. The following values were used in the calculations: refractive index of water equal to 1.333, viscosity of water equal to 0.890 centipoise, and refractive index of the zirconia particles equal to 1.9.

Two particle size measurements were calculated based on the PCS data. The intensity-average particle size, reported in nanometers, was equal to the size of a particle corresponding to the mean value of the scattered light intensity distribution. The scattered light intensity was proportional to the sixth power of the particle diameter. The volume-average particle size, also reported in nanometers, was derived from a volume distribution that was calculated from the scattered light intensity distribution taking into account both the refractive index of the zirconia particles and the refractive index of the dispersing medium (i.e., water). The volume-average particle size was equal to the particle size corresponding to the mean of the volume distribution.

The intensity-average particle size was divided by the volume-average particle size to provide a ratio that is indicative of the particle size distribution.

Crystalline Structure and Size (XRD Analysis) of Zirconia Particles in Zirconia Sol The particle size of a dried zirconia sample was reduced by hand grinding using an agate mortar and pestle. A liberal amount of the sample was applied by spatula to a glass microscope slide on which a section of double coated tape had been adhered. The sample was pressed into the adhesive on the tape by forcing the sample against the tape with the spatula blade. Excess sample was removed by scraping the sample area with the edge of the spatula blade, leaving a thin layer of particles adhered to the adhesive. Loosely adhered materials remaining after the scraping were remove by forcefully tapping the microscope slide against a hard surface. In a similar manner, corundum (Linde 1.0 µm alumina polishing powder, Lot Number C062, Union Carbide, Indianapolis, Ind.) was prepared and used to calibrate the diffractometer for instrumental broadening.

X-ray diffraction scans were obtained using a Philips vertical diffractometer having a reflection geometry, copper $K_\alpha$ radiation, and proportional detector registry of the scattered radiation. The diffractometer was fitted with variable incident beam slits, fixed diffracted beam slits, and graphite diffracted beam monochromator. The survey scan was conducted from 25 to 55 degrees (2θ) using a 0.04 degree step size and 8 second dwell time. X-ray generator settings of 45 kV and 35 mA were employed. Data collections for the corundum standard were conducted on three separate areas of several individual corundum mounts. Data was collected on three separate areas of the thin layer sample mount.

The observed diffraction peaks were identified by comparison to the reference diffraction patterns contained within the International Center for Diffraction Data (ICDD) powder diffraction database (sets 1-47, ICDD, Newton Square, Pa.) and attributed to either cubic/tetragonal (C/T) or monoclinic (M) forms of zirconia. The (111) peak for the cubic phase and (101) peak for the tetragonal phase were reported together. The amounts of each zirconia form were evaluated on a relative basis and the form of zirconia having the most intense diffraction peak was assigned the relative intensity value of 100. The strongest line of the remaining crystalline zirconia form was scaled relative to the most intense line and given a value between 1 and 100.

Peak widths for the observed diffraction maxima due to corundum were measured by profile fitting. The relationship between mean corundum peak widths and corundum peak position (2θ) was determined by fitting a polynomial to these data to produce a continuous function used to evaluate the instrumental breadth at any peak position within the corundum testing range. Peak widths for the observed diffraction maxima due to zirconia were measured by profile fitting observed diffraction peaks. The following peak widths were evaluated depending on the zirconia phase found to be present:

Cubic/Tetragonal (C/T): (1 1 1)
Monoclinic (M): (-1 1 1), and (1 1 1)

A Pearson VII peak shape model with $K_{\alpha 1}$ and $K_{\alpha 2}$ wavelength components accounted for, and linear background model were employed in all cases. Widths were found as the peak full width at half maximum (FWHM) having units of degrees. The profile fitting was accomplished by use of the capabilities of the JADE diffraction software suite. Sample peak widths were evaluated for the three separate data collections obtained for the same thin layer sample mount.

Sample peaks were corrected for instrumental broadening by interpolation of instrumental breadth values from corundum instrument calibration and corrected peak widths converted to units of radians. The Scherrer equation was used to calculate the primary crystal size.

$$\text{Crystallite Size } (D) = K\lambda/\beta(\cos\theta)$$

In the Scherrer equation,
K=form factor (here 0.9);
λ=wavelength (1.540598 Å);
β=calculated peak width after correction for instrumental broadening (in radians)=[calculated peak FWHM–instrumental breadth] (converted to radians) where FWHM is full width at half maximum; and
θ=½ the peak position (scattering angle).

The cubic/tetragonal crystallite size was measured as the average of three measurements using (1 1 1) peak.

$$\text{Cubic/Tetragonal Mean Crystallite Size} = [D(111)_{area\ 1} + D(111)_{area\ 2} + D(111)_{area\ 3}]/3$$

The monoclinic crystallite size was measured as the average of three measurement using the (-1 1 1) peak and three measurements using the (1 1 1) peak.

$$\text{Monoclinic Mean Crystallite Size} = [D(-111)_{area\ 1} + D(-111)_{area\ 2} + D(-111)_{area\ 3} + D(111)_{area\ 1} + D(111)_{area\ 2} + D(111)_{area\ 3}]/6$$

The weighted average of the cubic/tetragonal (C/T) and monoclininc phases (M) were calculated.

$$\text{Weighted average} = [(\% C/T)(C/T \text{ size}) + (\% M)(M \text{ size})]/100$$

In this equation,
%C/T=the percent crystallinity contributed by the cubic and tetragonal crystallite content of the $ZrO_2$ particles;
C/T size=the size of the cubic and tetragonal crystallites;
%M=the percent crystallinity contributed by the monoclinic crystallite content of the $ZrO_2$ particles; and
M size=the size of the monoclinic crystallites.

X-ray Diffraction Pattern Analysis for Sintered Bodies
Sample Preparation

Samples were placed on a zero background specimen holder composed of single crystal quartz. Samples were mixed with a silicon internal standard and applied to the specimen holder as a MEK slurry.

Data Collection

Reflection geometry data were collected in the form of a survey scan by use of a Philips vertical diffractometer, copper $K_\alpha$ radiation, and proportional detector registry of the scattered radiation. The diffractometer is fitted with variable incident beam slits, fixed diffracted beam slits, and graphite diffracted beam monochromator. The survey scan was conducted from 68 to 78 degrees (two theta) using a 0.02 degree step size and 90 second dwell time. X-ray generator settings of 45 kV and 35 mA were employed. Resulting data were subjected to profile fitting using a Pearson VII peak shape model to determine silicon and zirconia peak positions. Zirconia peak positions were corrected for sample transparency and displacement using the positions of the silicon (400) and (331) maxima. For calculation of zirconia lattice parameters, cubic phase (400) peak, tetragonal (220), and tetragonal (400) peaks were employed, as appropriate.

Dispersion Index

The Dispersion Index is equal to the volume-average size measured by PCS divided by the weighted average crystallite size measured by XRD.

Weight Percent Solids

The weight percent solids were determined by drying a sample weighing 3 to 6 grams at 120° C. for 30 minutes. The percent solids can be calculated from the weight of the wet sample (i.e., weight before drying, $\text{weight}_{wet}$) and the weight of the dry sample (i.e., weight after drying, $\text{weight}_{dry}$) using the following equation.

$$\text{wt-\% solids} = 100(\text{weight}_{dry})/\text{weight}_{wet}$$

Thermal Gravimetric Analysis (TGA)

The percent conversion of the zirconium-containing intermediate and the weight percent inorganic oxides were determined by thermal gravimetric analysis using a Model 2950 TGA from TA Instruments (New Castle, Del.).

To determine the percent conversion of the zirconium containing intermediate, a sample (e.g., 3 to 6 grams) was initially heated at 120° C. in an oven for 30 minutes to dry. The dried sample (e.g., 30 to 60 mg) was equilibrated at 85° C. in the TGA. The temperature was then increased at a rate of 20° C./minute to 200° C., held at 200° C. for 20 minutes, increased at 20° C./minute to 900° C., and held at 900° C. for 20 minutes. The organic material was volatilized between 200° C. and 900° C. leaving only the inorganic oxides such as $ZrO_2$ and $Y_2O_3$. The percent weight loss was calculated using the following equation.

$$\% \text{ weight loss} = 100(\%\text{-weight}_{200C} - \%\text{-weight}_{900C})/\%\text{-weight}_{900C}$$

The %-$\text{weight}_{200C}$ was calculated from the weight of the sample at 200° C. ($\text{weight}_{200C}$) and from the weight of the dried sample ($\text{weight}_{dry}$) used for the analysis (e.g., sample dried at 120° C. before analysis).

$$\%\text{-weight}_{200C} = 100(\text{weight}_{200C})/\text{weight}_{dry}$$

The %-weight$_{900C}$ is calculated from the weight of the sample at 900° C. (weight$_{900C}$) and from the weight of the dried sample (weight$_{dry}$) used for the analysis (e.g., sample dried at 120° C. before analysis.

$$\text{\%-weight}_{900C} = 100(\text{weight}_{900C})/\text{weight}_{dry}$$

The percent conversion of the zirconium-containing intermediate is given by the following equation $$\text{\% Conversion} = 100(A-B)/(A-C)$$

where A is the percent weight loss of the first feedstock, B is the percent weight loss of the zirconium-containing intermediate, and C is the percent weight loss of the zirconia sol.

The weight percent inorganic oxide was calculated from the weight percent solids and the weight percent oxide at 900° C. That is, the weight percent inorganic oxide can be calculated using the following equation.

$$\text{wt-\% inorganic oxides} = (\text{wt-\% solids})(\text{\%-weight}_{900C})/100$$

Index of Refraction

The refractive index was measured using an Abbe refractometer commercially available from Milton Roy Co. (Ivyland, Pa.).

Example 1

Preparation of a Zirconia Body in a Flexible Mold

The open top of a beaker was covered with flexible thermoplastic film (available under the trade designation PARAFILM M). A depression was formed in the film and this depression was filled with a zirconia sol prepared essentially as described in U.S. Patent Application Publication No. 2006/0148950. The zirconia sol was allowed to dry by evaporation at room temperature to afford a zirconia green body. The zirconia green body was then sintered by heating it in a furnace. The temperature of the furnace was increased at a rate of 5° C. per minute to a temperature of 900° C. The furnace temperature was held at 900° C. for ten minutes, and then the furnace heater was turned off and the furnace was allowed to cool to room temperature. Analysis of the sintered zirconia body by XRD analysis, as described above, indicated that tetragonal zirconia was the predominate phase in the body. The sintered zirconia was observed to be translucent.

Example 2

Preparation of a Zirconia Body in a Rigid Mold

A mold of a cylinder, the cylinder having a diameter of 3.8 centimeters (1.5 inches) and a length of approximately 10 centimeters (approximately 4 inches) with a 1.3 centimeter (0.5 inch) diameter hole in it, was prepared using dental plaster. After the plaster was set, the mold was dried at room temperature for one day. The mold was then filled with a zirconia sol prepared essentially as described in U.S. Patent Application Publication No. 2006/0148950. The zirconia sol was allowed to dry by evaporation at room temperature, and was continually replenished as it dried, to afford a zirconia green body having the cylindrical shape of the mold cavity and a length of approximately 1.3 centimeters (0.5 inch). The mold was broken into several pieces to remove the zirconia green body from it. The zirconia green body broke into several pieces during this removal step. The pieces of the zirconia green body were then sintered essentially as described in Example 1. Analysis of the sintered zirconia body pieces by XRD analysis, as described above, indicated that tetragonal zirconia was the predominate phase. The sintered zirconia was observed to be translucent.

Example 3

Preparation of a Zirconia Body in Sheet Form

Figure 2:
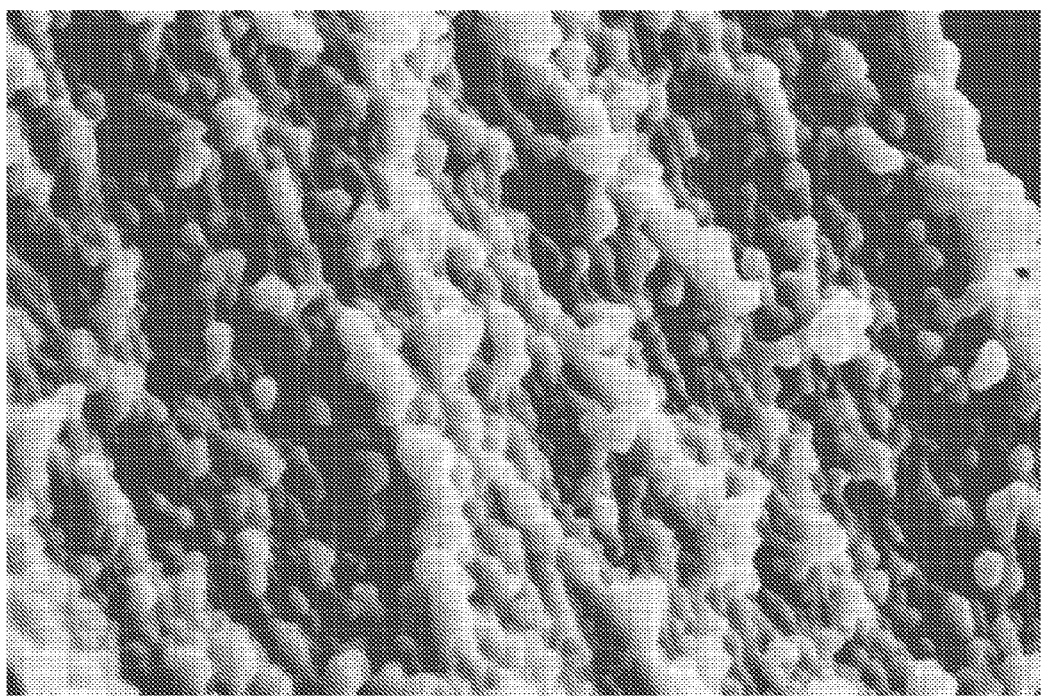
FIG. 2 is a scanning electron microscopy (SEM) image of an exemplary translucent sintered zirconia body.

A zirconia sol prepared essentially as described in U.S. Patent Application Publication No. 2006/0148950 was poured into a Petri dish in an amount sufficient to cover the bottom of the dish. The Petri dish was placed in a convection oven at 80° C., and the zirconia sol was dried to a sheet, which cracked into small flakes during drying. The flakes were then transferred to a crucible and sintered in a muffle furnace by heating to 900° C. at a rate of 10° C./minute. After cooling to room temperature, the flakes were imaged by SEM as shown in FIG. 2. The SEM image showed that the flakes were sintered bodies in which the nano-particle size was maintained.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What we claim is:

1. A method of making a translucent zirconia sintered body comprising:
   providing a zirconia sol comprising zirconia particles having an average primary particle size no greater than 50 nm;
   drying the zirconia sol to provide the zirconia green body; wherein the zirconia green body comprises primary particles and has a density of at least 50 percent of full density, the primary particles having:
      a major phase which is tetragonal zirconium oxide, and
      a size no greater than 50 nm; and
   wherein the diameter of any pores which are present in the green body is not more than about 30 nm; and
   sintering the zirconia green body at a temperature no greater than 1200° C. to provide a translucent zirconia sintered body comprised of primary particles and having a density of at least 99 percent of full density, the primary particles having:
      a major phase which is tetragonal zirconium oxide, and
      a size no greater than 100 nm; and
   wherein the diameter of any pores which are present in the translucent zirconia sintered body is not more than about 25 nm.

2. The method of claim 1 wherein
   drying the zirconia sol to provide the zirconia green body occurs by evaporation at room temperature.

3. The method of claim 2 wherein the zirconia particles have a dispersion index of 1 to 3, a ratio of intensity-average particle size to volume-average particle size no greater than 3.0, and a crystal structure that is at least 70 percent tetragonal.

4. The method of claim 2 further including a sintering additive with the zirconia sol, wherein the sintering additive is selected from the group consisting of aluminum, niobium, calcium, and oxides thereof.

5. The method of claim 2 wherein drying the zirconia sol is carried out in a mold.

6. The method of claim 1 wherein a temperature no greater than 1000° C. is used during sintering.

7. A method of making a dental article comprising:
providing a zirconia sol comprising zirconia particles having an average primary particle size no greater than 50 nm;
drying the zirconia sol to provide the zirconia green body;
sintering the zirconia green body to provide a translucent zirconia sintered body comprised of primary particles and having a density of at least 99 percent of full density, the primary particles having:
a major phase which is tetragonal zirconium oxide, and a size no greater than 100 nm; and
wherein the diameter of any pores which are present is not more than about 25 nm; and
shaping the translucent zirconia sintered body to provide a dental article.

8. The method of claim 7 wherein the major phase which is tetragonal zirconium oxide comprises at least 70 percent of the zirconium oxide in the primary particles.

9. The method of claim 7 wherein shaping the translucent zirconia sintered body is carried out by milling.

10. The method of claim 7 wherein drying the zirconia sol to provide the zirconia green body occurs by evaporation at room temperature.

11. A method of making a dental article comprising:
providing a zirconia sol comprising zirconia particles having an average primary particle size no greater than 50 nm;
drying the zirconia sol to provide the zirconia green body;
wherein the zirconia green body comprises primary particles and has a density of at least 50 percent of full density, the primary particles having:
a major phase which is tetragonal zirconium oxide, and a size no greater than 50 nm; and
wherein the diameter of any pores which are present in the zirconia green body is not more than about 30 nm;
sintering the zirconia green body at a temperature no greater than 1200° C. and for a time sufficient to form a partially sintered zirconia green body;
shaping the partially sintered zirconia green body; and
sintering the shaped, partially-sintered zirconia green body to provide a dental article comprising a shaped, translucent zirconia sintered body comprised of primary particles and having a density of at least 99 percent of full density, the primary particles having:
a major phase which is tetragonal zirconium oxide, and a size no greater than 100 nm; and
wherein the diameter of any pores which are present in the shaped, translucent zirconia sintered body is not more than about 25 nm.

12. The method of claim 11 wherein sintering the zirconia green body is carried out at a temperature no greater than 1000° C. and for a time sufficient to form a partially-sintered zirconia green body.

13. The method of claim 11 wherein the major phase which is tetragonal zirconium oxide comprises at least 70 percent of the zirconium oxide in the primary particles of the translucent zirconia sintered body.

14. The method of claim 11 wherein drying the zirconia sol to provide the zirconia green body occurs by evaporation at room temperature.

* * * * *